United States Patent [19]

Yoshizawa et al.

[11] Patent Number: 5,731,440
[45] Date of Patent: Mar. 24, 1998

[54] INTERMEDIATES FOR PRODUCING 5,7-DICHLORO-4-HYDROXYQUINOLINE

[75] Inventors: Hiroshi Yoshizawa; Motohiko Hamaguchi, both of Yokkaichi; Tomizo Fujino, Akashi, all of Japan

[73] Assignees: Ishihara Sangyo Kaisha Ltd., Osaka; Chemipro Kasei Kaisha, Ltd., Kobe, both of Japan

[21] Appl. No.: 700,363

[22] PCT Filed: Feb. 27, 1995

[86] PCT No.: PCT/JP95/00293

§ 371 Date: Sep. 3, 1996

§ 102(e) Date: Sep. 3, 1996

[87] PCT Pub. No.: WO95/23787

PCT Pub. Date: Sep. 8, 1995

[30] Foreign Application Priority Data

Mar. 1, 1994 [JP] Japan .................. 6-054410
Mar. 1, 1994 [JP] Japan .................. 6-054411

[51] Int. Cl.$^6$ .................. C07D 215/233; C07C 229/30
[52] U.S. Cl. .................. 546/156; 560/43; 560/44
[58] Field of Search .................. 546/153, 156; 558/395; 560/43, 44

[56] References Cited

U.S. PATENT DOCUMENTS

| | | | |
|---|---|---|---|
| 3,981,717 | 9/1976 | Walworth | 504/312 |
| 4,035,368 | 7/1977 | Erickson | 260/288 CE |
| 4,380,632 | 4/1983 | Steffen | 544/279 |
| 4,412,076 | 10/1983 | Baudouin | 546/153 |
| 5,081,121 | 1/1992 | Osawa | 514/312 |

FOREIGN PATENT DOCUMENTS 2537140  6/1984  France.

OTHER PUBLICATIONS

Savini L, Massarelli P, Pellerano C, Bruni G. Farmaco 48 (6), 805-25 (Abstract), 1993.

March J. Advanced Organic Chemistry. Second Eidtion. McGraw-Hill Book Company. New York. p. 514, 1977.

Primary Examiner—C. Warren Ivy
Assistant Examiner—Evelyn Huang
Attorney, Agent, or Firm—Oblon, Spivak, McClelland, Maier & Neustadt, P.C.

[57] ABSTRACT

An industrially advantageous process for producing 5,7-dichloro-4-hydroxyquinoline (DCHQ) useful as an intermediate for agrohorticultural bactericides. The process comprises (i) hydrolyzing 3-cyano- or 3-ethoxycarbonyl-5,7-dichloro-4-hydroxyquinoline into 5,7-dichloro-3-carboxy-4-hydroxyquinoline (DCQA) in the presence of hydrochloric, sulfuric or phosphoric acid and (ii) decarboxylating the formed DCQA into DCHQ in the presence of sulfuric or phosphoric acid. In particular, this process comprises continuously conducting the hydrolysis of 5,7-dichloro-3-ethoxycarbonyl-4-hydroxyquinoline and the decarboxylation of the hydrolyzate in the presence of sulfuric acid having a specified concentration. The invention also relates to a process for producing DCQA by hydrolyzing 3-cyano- or 3-ethoxycarbonyl-5,7-dichloro-4-hydroxyquinoline in the presence of hydrochloric, sulfuric or phosphoric acid and a process for producing DCHQ by decarboxylating DCQA in the presence of sulfuric or phosphoric acid.

2 Claims, No Drawings

5,731,440

1

INTERMEDIATES FOR PRODUCING 5,7-DICHLORO-4-HYDROXYQUINOLINE

This application is the national phase of PCT/JP95/00293, filed Feb. 27, 1995.

TECHNICAL FIELD

The present invention relates to a process for producing 5,7-dichloro-4-hydroxyquinoline (hereinafter, referred to as DCHQ) by decarboxylating 5,7-dichloro-3-carboxy-4-hydroxyquinoline (hereinafter, referred to as DCQA) in the presence of an acid; to a process for producing DCQA by hydrolyzing 3-cyano- or 3-ethoxycarbonyl-5,7-dichloro-4-hydroxyquinoline in the presence of an acid; to a process for producing DCHQ by successively decarboxylating DCQA formed in the above hydrolysis in the presence of an acid; and to certain intermediates for those manufacturing processes.

BACKGROUND ART

Japanese Unexamined Patent Publication No. Hei 1-246263 (JP Laid Open Appln. No. 246263/1989) discloses that 5,7-dichloro-4-(4-fluorophenoxy)quinoline shows an excellent plant fungicidal activity as an agrohorticultural bactericide. With respect to a process for producing said 5,7-dichloro-4-(4-fluorophenoxy)quinoline, there is disclosed a manufacturing process wherein a reaction product of 3,5-dichloroaniline and Meldrum's acid is heated to produce DCHQ, the resulting DCHQ is made to react with phosphorus oxychloride to produce 4,5,7-trichloroquinoline and the resulting 4,5,7-trichloroquinoline is made to react with 4-fluorophenol. In the manufacture of DCHQ in the above-mentioned process, it is usually conducted that 3,5-dichloroaniline is made to react with Meldrum's acid to produce 2,2-dimethyl-4,6-dioxo-5-(3,5-dichloroanilinomethylene)-1,3-dioxane and the resulting 2,2-dimethyl-4,6-dioxo-5-(3,5-dichloroanilinomethylene)-1,3-dioxane is thermally cyclized to give DCHQ. In addition to said process, it is also conducted, for example, that 3,5-dichloroaniline is made to react with diethyl ethoxymethylenemalonate to produce 5,7-dichloro-3-ethoxycarbonyl-4-hydroxyquinoline, the resulting 5,7-dichloro-3-ethoxycarbonyl-4-hydroxyquinoline is hydrolyzed with an aqueous solution of sodium hydroxide to produce DCQA and the resulting DCQA is decarboxylated on heating at 240°–250° C. to give DCHQ.

However, in the prior art processes, there are difficulties in their industrial utilizations that (i) especially in hydrolysis of 5,7-dichloro-3-ethoxycarbonyl-4-hydroxyquinoline, although the reaction time is short, the produced DCQA is of a very fine crystal whereby its separation is difficult resulting in a poor productivity; and (ii) the process requires a large quantity of heating medium for decarboxylation of DCQA. In addition, it is difficult to obtain a large amount of Meldrum's acid in low cost. Therefore, there has been a demand for a manufacturing process which is suitable for industrial utilization using a material available easier than Meldrum's acid.

The present inventors have conducted an investigation for overcoming the difficulties in the prior art processes, particularly the drawback which is inherent in the prior art process where diethyl ethoxymethylenemalonate is used, with particular attention for an improvement in effectively conducting the hydrolysis of 5,7-dichloro-3-ethoxycarbonyl-4-hydroxyquinoline and the decarboxylation of DCQA and also in conducting the decarboxylation of

2

DCQA without the use of heating medium whereupon a process for producing DCHQ which is suitable for industrial utilization has been achieved.

DISCLOSURE OF THE INVENTION

One aspect of the present invention is:

(i) a process for producing 5,7-dichloro-4-hydroxyquinoline (DCHQ) which comprises decarboxylating 5,7-dichloro-3-carboxy-4-hydroxyquinoline (DCQA) in the presence of sulfuric acid or phosphoric acid;

(ii) a process for producing DCHQ which comprises hydrolyzing 3-cyano- or 3-ethoxycarbonyl-5,7-dichloro-4-hydroxyquinoline in the presence of hydrochloric acid, sulfuric acid or phosphoric acid followed by subjecting the resulting 5,7-dichloro-3-carboxy-4-hydroxyquinoline (DCQA) to a decarboxylation as mentioned in the above process (i); and (iii) a process for producing DCHQ according to the above-mentioned process (ii) in which hydrolysis and decarboxylation are continuously conducted in the presence of sulfuric acid or phosphoric acid.

Another aspect of the present invention is:

(iv) a process of producing DCQA which comprises hydrolyzing 3-cyano- or 3-ethoxycarbonyl-5,7-dichloro-4-hydroxyquinoline in the presence of hydrochloric acid, sulfuric acid or phosphoric acid;

(v) a process of producing DCHQ which comprises (a) condensing 3,5-dichloroaniline with ethyl orthoformate or ethyl cyanoacetate, (b) subjecting the resulting ethyl 1-cyano-2-(3,5-dichloroanilino)acrylate to a thermal cyclization and (c) then subjecting the resulting 3-cyano-5,7-dichloro-4-hydroxyquinoline to the above-mentioned process (ii) or (iv) and;

(vi) certain intermediates for the above-mentioned producing processes.

According to those processes, crystals of DCQA can be easily separated from the reaction products of the hydrolysis and also DCQA can be favorably decarboxylated without a heating medium. Furthermore, there is no need of separating the DCQA after hydrolysis but decarboxylation can be continuously carried out. Thus, many advantages can be resulted for the industrial utilization.

DETAILED DESCRIPTION OF THE INVENTION 5,7-Dichloro-3-ethoxycarbonyl-4-hydroxyquinoline which is used as a starting material in the process of the present invention may be readily manufactured by thermal cyclization of a reaction product of 3,5-dichloroaniline with diethyl ethoxymethylenemalonate. It is also possible to readily manufacture 5,7-dichloro-3-cyano-4-hydroxyquinoline by thermal cyclization of a reaction product of 3,5-dichloroaniline with ethyl orthoformate and ethyl cyanoacetate.

Production of 3-cyano- or 3-acetyl-5,7-dichloro-4-hydroxyquinoline is generally conducted as follows:

3,5-Dichloroaniline, ethyl orthoformate and ethyl cyanoacetate or ethyl acetoacetate which are all easily available in industry are used as starting materials for the instant process and, generally, those materials are thermally condensed in the presence of a heating medium which is inert to the reaction and in an atmosphere of nitrogen gas. Amounts of those materials used are not necessarily specified because they are dependent upon the reaction conditions and reaction devices but, usually, 0.8–3.0 moles (preferably, 1.0–1.5 moles) of ethyl orthoformate and 0.8–3.0 moles of ethyl cyanoacetate or ethyl acetoacetate (preferably, 1.0–1.5 moles of ethyl cyanoacetate) are used to one mole of 3,5-dichloroaniline. Reaction temperature is usually from 70° to 200° C., and preferably from 90° to 170° C.

The above-mentioned heating medium may include those which are inert to the reaction, those which are not decomposed in the condensation and the like. Examples of the above-mentioned heating medium are alkylnaphthalenes, diphenyl, diphenyl ether, alkyl diphenyls, triphenyl hydride, etc. They may be used either solely or jointly. More specific examples are Therm-S 200, 300, 600, 700, 800 and 900 (trade names; manufactured by Nippon Steel Chemical Co., Japan) and Dowtherm A (trade name; manufactured by The Dow Chemical Co., USA). Among them, Therm-S 300 (trade name; manufactured by Nippon Steel Chemical Co., Japan) and Dowtherm A (trade name; manufactured by The Dow Chemical Co., USA) are preferred. Amounts of the heating medium are not necessarily specified but, usually, from 50 to 500 parts by weight, and preferably from 100 to 260 parts by weight, to 100 parts by weight of 3,5-dichloroaniline.

As a condensation proceeds, ethanol is usually by-produced and it is removed outside of the reaction system by evaporation. As such, the condensation usually finishes within from 3 to 15 hours to give ethyl 1-cyano-2-(3,5-dichloroanilino)acrylate or ethyl 1-acetyl-2-(3,5-dichloroanilino)acrylate. The condensation product is subjected to conventional steps of purification and separation whereupon the above-mentioned acrylate can be readily obtained. Thus, for example, the condensation product is crystallized by diluting with a solvent such as ethanol or isopropanol. Then the crystals of the acrylate separated out therefrom were filtered, if necessary, followed by washing with the above-mentioned solvent to give said acrylate with a high purity.

Next, ethyl 1-cyano- or ethyl 1-acetyl-2-(3,5-dichloroanilino)acrylate is thermally cyclized to give 3-cyano- or 3-acetyl-5,7-dichloro-4-hydroxyquinoline. Cyclization is usually conducted in the presence of a heating medium. Thus, for example, the acrylate is added either gradually or in portions to a previously-heated heating medium with stirring and the reaction is conducted paying such an attention that the occurrence of the side reaction is made as little as possible throughout that period. With respect to a heating medium, those which are the same as those used in the above condensation may be used. The amount of the heating medium is not necessarily specified but it is usually from 200 to 2,000 parts by weight, and preferably from 500 to 1,500 parts by weight, to 100 parts by weight of the acrylate. The cyclization is usually conducted at the reaction temperature of 200°–260° C., and preferably at 240°–260° C. for 5–20 hours. The cyclization is carried out by removing the heating medium and by-produced ethanol from the reaction system by evaporation. Similarly to the case of the above-mentioned condensation product, when the cyclization product is subjected to the conventional purifying and separating steps, 3-cyano-5,7-dichloro-4-hydroxyquinoline or 3-acetyl-5,7-dichloro-4-hydroxyquinoline is readily obtained.

Alternatively, 3,5-dichloroaniline, ethyl orthoformate and ethyl cyanoacetate or ethyl acetoacetate may be thermally condensed so that the cyclization of the resulting condensation product is carried out continuously or simultaneously whereupon 3-cyano- or 3-acetyl-5,7-dichloro-4-hydroxyquinoline is obtained favorably. In that case, the reaction may be carried out without isolation and purification of the condensation product, and/or with care so that occurrence of the side reaction is made as little as possible. Amounts of the starting materials and their ratio, heating temperature, type and amount of the heating medium used, etc. may be suitably selected. When 3-cyano-5,7-dichloro-4-hydroxyquinoline is subjected to hydrolysis and decarboxylation in accordance with the present invention, it can be smoothly converted to DCHQ but 3-acetyl-5,7-dichloro-4-hydroxyquinoline can be also converted to DCHQ by subjecting to a deacetylation which is usually conducted for acetyl-substituted aromatic compounds.

In the present invention, 3-cyano- or 3-ethoxycarbonyl-5,7-dichloro-4-hydroxyquinoline is mixed with hydrochloric acid, sulfuric acid or phosphoric acid with heating whereupon the hydrolysis usually takes place. Concentration and amount of hydrochloric acid, sulfuric acid or phosphoric acid used here are not necessarily specified because of their dependency on type of the starting materials, reaction temperature, reaction device, etc. Usually, however, the concentration of hydrochloric acid is 5–35%, and preferably 20–35%, and that of sulfuric acid and phosphoric acid is 5–85%, and preferably 50–70%, while its amount to one mole of the starting 3-cyano- or 3-ethoxycarbonyl-5,7-dichloro-4-hydroxyquinoline is 3–50 moles, and preferably 3–25 moles. Temperature for the hydrolysis is not, again, necessarily specified but it is usually from 70° to 200° C., and preferably from 80° to 150° C. The reaction time is from 0.5 to 10 hours. When 3-cyano- or 3-ethoxycarbonyl-5,7-dichloro-4-hydroxyquinoline is used as a starting material and is hydrolyzed, ammonia or ethanol is by-produced, respectively but ammonia can be neutralized with the acid in the reaction system to give an ammonium salt of the acid while ethanol can be easily removed from the reaction system by distillation during the hydrolysis.

At the stage where hydrolysis is completed in the present invention, the resulting DCQA is once separated from the reaction products and then subjected either to a decarboxylation of DCQA or, without separating the DCQA, to a hydrolysis followed by a decarboxylation. When DCQA is separated from the reaction product, common purifying and separating operations may be applied to the hydrolysis products. Thus, for example, the reaction products are cooled, poured into water and stirred to produce crystals followed by subjecting to a simple solid-liquid separation to give DCQA smoothly.

In the present invention, the decarboxylation is usually conducted by mixing DCQA with sulfuric acid or phosphoric acid with heating. Concentration and amount of sulfuric acid or phosphoric acid are not necessarily specified but the concentration is usually from 5 to 85%, preferably from 50 to 85%, and more preferably from 50 to 70%, and the amount to one mole of DCQA is from 3 to 50 moles, and preferably from 3 to 25 moles. This decarboxylation is usually completed at 100°–200° C., and preferably at 120°–170° C., within 1–24 hours and, during the decarboxylation, carbon dioxide gas is removed from the reaction system.

In conducting the hydrolysis and decarboxylation in the process according to the present invention, a suitable combination of type, concentration and amount of the acid is selected. For example, the hydrolysis is carried out using diluted hydrochloric acid and then the decarboxylation is conducted using 50–70% sulfuric acid; the hydrolysis is carried out using 5–50% sulfuric acid or 5–50% phosphoric acid and then the decarboxylation is carried out using 50–70% sulfuric acid or 50–70% phosphoric acid by adding higher concentration of sulfuric acid or phosphoric acid thereto; or the hydrolysis and decarboxylation are continuously carried out using 50–70% sulfuric acid as from the initial stage. Among those three, the latter method is most preferred in view of reaction operations and reaction efficiency. When the decarboxylation product is subjected to common purifying and separating steps, desired DCHQ can be readily obtained. For example, the decarboxylation product is cooled and poured into water to crystallize the DCHQ and then the crystals are filtered and washed with water, with an aqueous alkali solution such as sodium hydroxide, potassium hydroxide, sodium carbonate and potassium carbonate, or with alcohol such as ethanol and isopropanol. As a result, the desired DCHQ can be recovered, for example, with a purity of 97% and with a yield of not less than 94%. In accordance with the present invention, it is also possible that said hydrolysis and decarboxylation are conducted in the same reaction system whereby the desired DCHQ is favorably obtained. Further in accordance with the present invention, the desired DCHQ may be also obtained favorably by conducting said hydrolysis and decarboxylation continuously for forming a heterogeneous reaction phase in the same reaction system.

EXAMPLES

Described below are examples of the present invention which are provided only for illustrative purposes.

Example 1. (Manufacture of 5,7-Dichloro-4-hydroxyquinoline)

5,7-Dichloro-3-ethoxycarbonyl-4-hydroxyquinoline (114.4 g; 0.4 mole) and 572 g of 62.5% sulfuric acid were charged in a 1,000 ml four-necked flask equipped with stirrer, thermometer and distilling tube and the mixture was heated with stirring at 120° C. Ethanol which was by-produced during the reaction was evaporated outside the reaction system and the reaction was conducted by heating the reactants at 140° C. for three hours. The reaction mixture was analyzed by means of liquid chromatography whereupon it was found that the starting 5,7-dichloro-3-ethoxycarbonyl-4-hydroxyquinoline disappeared while 5,7-dichloro-3-carboxy-4-hydroxyquinoline in 78% yield and 5,7-dichloro-4-hydroxyquinoline in 22% yield were produced.

After the distilling tube was changed to a reflux condenser and the reaction mixture was heated to 145°–150° C., the reaction was conducted by heating the reaction mixture for 12 hours more. The reaction products were analyzed by liquid chromatography whereupon it was found that 5,7-dichloro-3-carboxy-4-hydroxyquinoline disappeared while 5,7-dichloro-4-hydroxyquinoline in 99% yield was produced.

The reaction product was poured into 572 g of cold water to form crystals of 5,7-dichloro-4-hydroxyquinoline followed by filtration. The crystals were washed with water and dried to give 82.1 g of 5,7-dichloro-4-hydroxyquinoline (purity: 99%; yield: 95%).

Example 2. (Manufacture of 5,7-Dichloro-4-hydroxyquinoline) Manufacture of 5,7-Dichloro-3-cyano-4-hydroxyquinoline (A)

(A-1). Ethyl orthoformate (15.6 g; 0.1 mole), 12.2 g (0.1 mole) of ethyl cyanoacetate, 16.2 g (0.1 mole) of 3,5-dichloroaniline and 28 ml of Therm-S 300 (trade name; a heating medium; manufactured by Nippon Steel Chemical Co., Japan) were charged in a 300 ml four-necked flask and the mixture was stirred. The temperature of the mixture was elevated to 96° C. during one hour together with introduction of nitrogen gas, then gradually raised with evaporation of the generated ethanol and elevated up to 160° C. during about 1.5 hours more. The reaction was conducted at 160°–170° C. for 7 hours. The end point of the reaction was confirmed by analyzing the content in the flask by means of liquid chromatography. The reaction product was crystallized by diluting with 300 ml of isopropanol and the separated crystals were filtered at 25° C. and washed with 120 ml of isopropanol to give 25.6 g of ethyl 2-(3,5-dichloroanilino)-1-cyanoacrylate. Its melting point was 179°–180° C., the purity as analyzed by liquid chromatography was 99.99% and the yield based upon a 3,5-dichloroaniline group was 89.5%.

(A-2). Therm-S 300 (120 ml; a heating medium) was charged in a 300 ml four-necked flask equipped with a water separator and stirred. Into the stirred Therm-S 300 with heating at 253°–254° C. was poured 10 g (0.035 mole) of ethyl 2-(3,5-dichloroanilino)-1-cyanoacrylate in portions during seven hours and the reaction was continued by evaporating the heating medium and the by-products at 254°–255° C. for three hours more. The end point of the reaction was confirmed by liquid chromatography (distilled amount of ethanol was 8.2 ml). The reaction product was cooled at 90° C., crystallized by adding 30 ml of isopropanol thereto and the separated crystals were filtered at 20° C. and washed with 30 ml of isopropanol to give 8.2 g of 5,7-dichloro-3-cyano-4-hydroxyquinoline. This crystal was pale brown. The purity as a result of analysis by liquid chromatography was 98.1% and the yield based upon ethyl 2-(3,5-dichloroanilino)-1-cyanoacrylate was 98.1%.

Manufacture of 5,7-Dichloro-3-cyano-4-hydroxyquinoline (B)

(B-1). Ethyl orthoformate (15.6 g; 0.1 mole), 12.2 g (0.1 mole) of ethyl cyanoacetate, 16.2 g (0.1 mole) of 3,5-dichloroaniline and 42 ml of Therm-S 300 (a heating medium; trade name; manufactured by Nippon Steel Chemical Co., Japan) were charged in a 300 ml four-necked flask and the mixture stirred. The temperature of the mixture was elevated to 96° C. during one hour together with introduction of nitrogen gas, gradually raised together with evaporation of generating ethanol and elevated up to 160° C. during 1.5 hours more and the reaction was conducted at 160°–170° C. for seven hours. The end point of the reaction was confirmed by analyzing the content in the flask using liquid chromatography for checking the disappearance of the starting 3,5-dichloroaniline.

After completion of the reaction, the temperature in the flask was allowed to drop to 150° C. and low-boiling fractions (such as unreacted ethyl cyanoacetate) boiling together with Therm-S 300 were evaporated (distilled amount: 17 ml) whereupon a solution of ethyl 2-(3,5-dichloroanilino)-1-cyanoacrylate in Therm-S 300 was obtained. This solution was analyzed by liquid chromatography whereupon it contained 26.3 g of ethyl 2-(3,5-dichloroanilino)-1-cyanoacrylate (the yield based upon 3,5-dichloroaniline: 92%).

(B-2). Therm-S 300 (a heating medium) (316 ml) was charged in a 1,000 ml four-necked flask equipped with stirrer, thermometer and water separator and stirred. To the stirred Therm-S 300 was added dropwise a solution of ethyl 2-(3,5-dichloroanilino)-1-cyanoacrylate in Therm-S 300 prepared in the above (B-1) during ten hours with heating at 253°–254° C., and the reaction was further conducted by evaporating the heating medium and the by-products at 254°–255° C. for two hours. The end point of the reaction was confirmed by liquid chromatography. The end point of the reaction was checked by confirming the disappearance of ethyl 2-(3,5-dichloroanilino)-1-cyanoacrylate (Distilled amount including ethanol was 33 ml.). The reaction product was cooled at 90° C., crystallized by adding 80 ml of isopropanol thereto, cooled at 30° C., filtered and washed with 80 ml of isopropanol to give 21.5 g of 5,7-dichloro-3-cyano-4-hydroxyquinoline. This crystal was pale brown and its purity analyzed by liquid chromatography was 97.8% while its yield based upon 3,5-dichloroaniline was 90.0%.

Manufacture of 5,7-Dichloro-4-hydroxyquinoline 5,7-Dichloro-3-cyano-4-hydroxyquinoline (7.0 g; 0.0293 mole) and 104 g of 62.5% sulfuric acid were charged in a 300 ml four-necked flask equipped with stirrer, thermometer and reflux condenser, and the mixture was heated up to a boiling point (144°–146° C.) during one hour and subjected to a reaction at the same temperature for 15 hours. When the reaction product was analyzed by liquid chromatography, 5,7-dichloro-4-hydroxyquinoline was produced in 99% yield (where the starting 5,7-dichloro-3-cyano-4-hydroxyquinoline disappeared while an intermediate, 5,7-dichloro-3-carboxy-4-hydroxyquinoline, was produced in not more than 0.2% yield).

The reaction product was cooled to 110° C. and allowed to crystallize 5,7-dichloro-4-hydroxyquinoline by adding 104 g of water gradually thereto followed by filtering. The crystals were washed with water and further washed with 20 ml of isopropanol to give 5.93 g of 5,7-dichloro-4-hydroxyquinoline (purity: 99.88%; yield: 94.6%).

Example 3 (Manufacture of 5,7-Dichloro-4-hydroxyquinoline)

5,7-Dichloro-3-ethoxycarbonyl-4-hydroxyquinoline (114.4 g; 0.4 mole) and 343.2 g of 70% sulfuric acid were charged in a 1,000 ml four-necked flask equipped with stirrer, thermometer and distilling tube and the mixture was heated at 150° C. with stirring. Reaction was continued by heating up to 165° C. during three hours together with evaporation of the by-produced ethanol outside the reaction system. The reaction product was analyzed by liquid chromatography whereupon and it was found that the starting 5,7-dichloro-3-ethoxycarbonyl-4-hydroxy-quinoline disappeared and that 5,7-dichloro-3-carboxy-4-hydroxyquinoline in 22% yield and 5,7-dichloro-4-hydroxyquinoline in 78% yield were produced.

After the distilling tube was changed to a reflux condenser and the reaction mixture was heated to 165°–175° C., the reaction was conducted with heating for seven hours more. The reaction product was analyzed by liquid chromatography whereupon 5,7-dichloro-3-carboxy-4-hydroxyquinoline disappeared and 5,7-dichloro-4-hydroxyquinoline was produced in 99% yield.

The reaction product was cooled to 100° C., crystallized by adding 258 g of water gradually thereto, cooled to 30° C. and filtered. The crystals were poured into 600 g of water, heated at 40°–45° C., neutralized with aqueous 48% sodium hydroxide with stirring to pH 3–4, filtered at 30° C., washed with water, further washed with 80 ml of isopropanol and dried to give 84.0 g of 5,7-dichloro-4-hydroxyquinoline (purity: 99%; yield: 98%).

Example 4. (Manufacture of 5,7-Dichloro-3-acetyl-4-hydroxyquinoline)

(1) The same operations as in Example 2 (A-1) were conducted for the manufacture of 5,7-dichloro-3-cyano-4-hydroxyquinoline (A) in the above-mentioned Example 2 except that 13 g (0.1 mole) of ethyl acetoacetate was used instead of 12.2 g (0.1 mole) of ethyl cyanoacetate to give 26.0 g of ethyl 2-(3,5-dichloroanilino)-1-acetylacrylate. The purity of this product analyzed by liquid chromatography was 98.9% and the yield based upon 3,5-dichloroaniline was 86.0%.

(2) Then the same operations as in Example 2 (A-2) were conducted except that 10.6 g (0.035 mole) of ethyl 2-(3,5-dichloroanilino)-1-acetylacrylate was added in a divided manner during six hours instead of 10 g (0.035 mole) of ethyl 2-(3,5-dichloroanilino)-1-cyanoacrylate of Example 2 (A-2) to give 8.7 g of 5,7-dichloro-3-acetyl-4-hydroxyquinoline. This crystal was pale yellow and the purity analyzed by liquid chromatography was 99.0% while the yield based upon 2-(3,5-dichloroanilino)-1-acetylacrylate was 97.0%.

MERIT OF THE INVENTION

In accordance with the present invention, 3-cyano- or 3-ethoxycarbonyl-5,7-dichloro-4-hydroxyquinoline is hydrolyzed in the presence of hydrochloric acid, sulfuric acid or phosphoric acid to give 5,7-dichloro-3-carboxy-4-hydroxyquinoline (DCQA) and, when the resulting product is decarboxylated in the presence of sulfuric acid or phosphoric acid, 5,7-dichloro-4-hydroxyquinoline (DCHQ) can be readily manufactured. In the present invention, DCQA can be smoothly and advantageously separated from the hydrolysis intermediates. Moreover, there is no need of using a heating medium in the decarboxylation. It is also possible that both hydrolyzing and decarboxylating reactions can be continuously carried out without separating 5,7-dichloro-3-carboxy-4-hydroxyquinoline during the reactions.

We claim:
1. 3-acetyl-5,7-dichloro-4-hydroxyquinoline.
2. Ethyl 1-acetyl-2-(3,5-dichloroanilino)acrylate.

* * * * *